(12) United States Patent
Becker et al.

(10) Patent No.: US 7,005,556 B1
(45) Date of Patent: Feb. 28, 2006

(54) MULTILAYER WOUND DRESSING

(75) Inventors: Robert O. Becker, Lowville, NY (US);
A. Bartholomew Flick, Lakemont, GA (US); Adam J. Becker, Scarsdale, NY (US)

(73) Assignee: Argentum Medical, Chicago, IL (US)

( * ) Notice: Subject to any disclaimer, the term of this patent is extended or adjusted under 35 U.S.C. 154(b) by 0 days.

(21) Appl. No.: 08/707,779

(22) Filed: Sep. 3, 1996

Related U.S. Application Data

(63) Continuation-in-part of application No. 08/524,134, filed on Sep. 5, 1995, now abandoned, which is a continuation-in-part of application No. 08/623,046, filed on Mar. 28, 1996, now Pat. No. 5,814,094.

(51) Int. Cl.
*A61F 13/00* (2006.01)

(52) U.S. Cl. .............................. 602/48; 602/43; 602/44; 424/447

(58) Field of Classification Search ............ 602/41–59; 424/443–449; 604/304–308, 20; 128/888
See application file for complete search history.

(56) References Cited

U.S. PATENT DOCUMENTS

| | | | |
|---|---|---|---|
| 2,934,066 A | 4/1960 | Stowasser | |
| 3,326,213 A | 6/1967 | Gallagher | 128/156 |
| 3,420,233 A | 1/1969 | Kanof | 128/260 |
| 3,596,657 A | 8/1971 | Eidus | 128/156 |
| 3,800,792 A | 4/1974 | McKnight et al. | |
| 3,830,908 A | 8/1974 | Klippel et al. | |
| 3,934,066 A | 1/1976 | Murch | 428/248 |
| 3,964,477 A | 6/1976 | Ellis et al. | 128/172.1 |
| 4,027,393 A | 6/1977 | Ellis et al. | 32/10 A |
| 4,034,750 A | 7/1977 | Seiderman | 128/155 |
| 4,142,521 A | 3/1979 | Konikoff | |
| 4,291,125 A | 9/1981 | Greatbatch | 435/240 |
| 4,297,995 A | 11/1981 | Golub | 128/156 |
| 4,313,438 A | 2/1982 | Greatbatch | 128/207.21 |
| 4,333,449 A | 6/1982 | Muller et al. | |
| 4,476,590 A | 10/1984 | Scales et al. | 3/1.91 |
| 4,486,488 A | 12/1984 | Pietsch et al. | |
| 4,528,265 A | 7/1985 | Becker | 435/172.1 |
| 4,529,623 A | 7/1985 | Maggs | 427/227 |
| 4,541,426 A * | 9/1985 | Webster | 602/42 |
| 4,551,139 A | 11/1985 | Plaas et al. | 604/290 |
| 4,563,184 A | 1/1986 | Korol | 604/368 |
| 4,600,001 A | 7/1986 | Gilman | 128/156 |
| 4,606,338 A | 8/1986 | Greenway et al. | 128/156 |

(Continued)

FOREIGN PATENT DOCUMENTS

EP    0 099 758    2/1984

(Continued)

OTHER PUBLICATIONS

R. O. Becker, et al., "Treatment of Orthopaedic Infections With Electrically Generated Silver Ions," *Journal of Bone & Joint Surgery*, vol. 60-A, pp. 871-881 (1978), USA, 1st named inventor is co-author.

(Continued)

*Primary Examiner*—Kim M. Lewis
(74) *Attorney, Agent, or Firm*—Merchant & Gould, LLC

(57) ABSTRACT

A flexible, multilayer wound dressing with antibacterial and antifungal properties, together with methods for making the dressing. The dressing includes a layer of silver-containing fabric, a layer of absorbent material, and (optionally) a layer of a flexible air-permeable and/or water-impermeable material. The dressing can be used for prophylactic and therapeutic care and treatment of skin infections and surface wounds (including surgical incisions), as a packing material, and as a swab for surface cleaning.

13 Claims, 2 Drawing Sheets

U.S. PATENT DOCUMENTS

| | | | |
|---|---|---|---|
| 4,615,705 A | 10/1986 | Scales et al. .................. 623/11 |
| 4,619,252 A | 10/1986 | Ibbott ........................ 128/82.1 |
| 4,635,624 A | 1/1987 | Gilman ........................ 128/156 |
| 4,646,730 A | 3/1987 | Schonfeld et al. .......... 728/156 |
| 4,654,323 A | 3/1987 | Beitner |
| 4,671,266 A | 6/1987 | Lengyel et al. ............. 128/156 |
| 4,728,323 A | 3/1988 | Matson |
| 4,747,845 A | 5/1988 | Korol ........................ 604/368 |
| 4,757,804 A | 7/1988 | Griffith et al. ............... 128/1.5 |
| 4,767,401 A | 8/1988 | Seiderman |
| 4,781,705 A | 11/1988 | Shepherd et al. ........... 604/289 |
| 4,798,603 A | 1/1989 | Meyer et al. ............... 604/378 |
| 4,817,594 A | 4/1989 | Juhasz |
| 4,818,697 A | 4/1989 | Liboff et al. ................. 435/173 |
| 4,825,877 A | 5/1989 | Kempe ........................ 128/846 |
| 4,847,049 A | 7/1989 | Yamamoto .................... 422/24 |
| 4,886,505 A | 12/1989 | Haynes et al. ............... 604/265 |
| 4,889,530 A | 12/1989 | Smith ........................ 604/304 |
| 4,909,244 A | 3/1990 | Quarfoot .................... 128/156 |
| 4,911,688 A | 3/1990 | Jones |
| 4,932,951 A | 6/1990 | Liboff et al. .................. 606/13 |
| 4,935,087 A | 6/1990 | Gilman ........................ 156/251 |
| 4,960,413 A | 10/1990 | Sagar et al. ................. 604/289 |
| 4,979,946 A | 12/1990 | Gilman ........................ 604/307 |
| 4,982,742 A | 1/1991 | Claude |
| 4,984,570 A | 1/1991 | Langen et al. ............... 128/156 |
| 4,990,144 A | 2/1991 | Blott ........................ 604/304 |
| 4,997,425 A | 3/1991 | Shioya et al. ............... 604/304 |
| 5,018,515 A | 5/1991 | Gilman ........................ 128/155 |
| 5,018,516 A | 5/1991 | Gilman ........................ 128/155 |
| 5,019,096 A | 5/1991 | Fox, Jr. et al. |
| 5,042,466 A | 8/1991 | McKnight .................... 128/155 |
| 5,049,139 A | 9/1991 | Gilchrist .................... 604/265 |
| 5,056,510 A | 10/1991 | Gilman ........................ 128/155 |
| 5,130,342 A | 7/1992 | McAllister et al. |
| 5,133,199 A | 7/1992 | Parikh et al. .................. 66/192 |
| 5,147,338 A | 9/1992 | Lang et al. ................. 604/304 |
| 5,147,344 A | 9/1992 | Sachau et al. |
| 5,158,555 A | 10/1992 | Porzilli ........................ 604/307 |
| 5,167,613 A | 12/1992 | Karami et al. ................ 602/42 |
| 5,180,585 A | 1/1993 | Jacobson et al. |
| 5,185,000 A | 2/1993 | Brandt et al. |
| 5,266,371 A | 11/1993 | Sugii et al. ..................... 428/40 |
| 5,288,544 A | 2/1994 | Mallen et al. |
| 5,292,589 A | 3/1994 | Shepherd et al. ........... 428/412 |
| 5,306,229 A | 4/1994 | Brandt et al. |
| 5,308,313 A | 5/1994 | Karami et al. ................ 602/55 |
| 5,320,908 A | 6/1994 | Sodervall et al. |
| 5,322,520 A | 6/1994 | Milder ........................ 604/265 |
| 5,324,275 A | 6/1994 | Raad et al. ................. 604/265 |
| 5,326,567 A | 7/1994 | Capelli |
| 5,333,753 A | 8/1994 | Etheredge .................... 221/33 |
| 5,340,363 A | 8/1994 | Fabo |
| 5,374,283 A | 12/1994 | Flick ........................ 607/46 |
| 5,405,644 A | 4/1995 | Ohsumi et al. |
| 5,413,788 A | 5/1995 | Edwards et al. |
| 5,419,161 A | 5/1995 | Bodenschatz et al. |
| 5,429,590 A | 7/1995 | Saito et al. .................. 602/48 |
| 5,429,591 A | 7/1995 | Yamamoto et al. ........... 602/54 |
| 5,454,886 A | 10/1995 | Burrell et al. ............... 148/565 |
| 5,465,735 A | 11/1995 | Patel ........................ 128/888 |
| 5,470,576 A | 11/1995 | Patel ........................ 424/445 |
| 5,470,585 A | 11/1995 | Gilchrist .................... 424/604 |
| 5,512,041 A | 4/1996 | Bogart ........................ 602/58 |
| 5,520,664 A | 5/1996 | Bricault et al. ............. 604/265 |
| 5,543,151 A | 8/1996 | Shirai et al. ................ 424/448 |
| 5,571,079 A | 11/1996 | Bello et al. .................. 602/46 |
| 5,571,521 A | 11/1996 | Lasker ........................ 424/409 |
| 5,595,750 A | 1/1997 | Jacobson et al. |
| 5,607,683 A | 3/1997 | Capelli ........................ 424/405 |
| 5,632,731 A | 5/1997 | Patel ........................ 602/59 |
| 5,662,913 A | 9/1997 | Capelli |
| 5,681,575 A | 10/1997 | Burrell et al. ............... 424/423 |
| 5,695,857 A | 12/1997 | Burrell et al. ............... 428/209 |
| 5,744,151 A | 4/1998 | Capelli |
| 5,753,251 A | 5/1998 | Burrell et al. ............... 424/426 |
| 5,770,255 A | 6/1998 | Burrell et al. ............... 427/2.1 |
| 5,772,620 A | 6/1998 | Szlema et al. |
| 5,779,659 A | 7/1998 | Allen ........................ 602/75 |
| 5,782,785 A | 7/1998 | Herzberg |
| 5,782,788 A | 7/1998 | Widemire .................... 602/48 |
| 5,814,094 A * | 9/1998 | Becker et al. ................. 607/50 |
| 5,824,267 A | 10/1998 | Kawasumi et al. |
| 5,836,970 A | 11/1998 | Pandit ........................ 606/213 |
| 5,844,013 A | 12/1998 | Kenndoff et al. |
| 5,921,948 A | 7/1999 | Kawaguchi et al. .......... 602/52 |
| 5,974,344 A | 10/1999 | Shoemaker, II ............. 607/149 |
| 5,985,301 A | 11/1999 | Nakamura et al. |
| 5,985,308 A | 11/1999 | Burrell et al. |
| 5,998,692 A | 12/1999 | Gilding |
| 6,004,667 A | 12/1999 | Sakurada et al. ........... 428/323 |
| 6,074,965 A | 6/2000 | Bodenschatz et al. |
| 6,087,549 A | 7/2000 | Flick ........................ 602/41 |
| 6,093,414 A | 7/2000 | Capelli |
| 6,099,489 A | 8/2000 | Herzberg et al. |
| 6,120,470 A | 9/2000 | Bodenschatz et al. |
| 6,129,694 A | 10/2000 | Bodenschatz |
| 6,139,856 A | 10/2000 | Kaminska et al. .......... 424/404 |
| 6,149,616 A | 11/2000 | Szlema et al. |
| 6,160,196 A | 12/2000 | Knieler et al. |
| 6,171,648 B1 | 1/2001 | Himmelsbach et al. |
| 6,180,544 B1 | 1/2001 | Jauchen et al. |
| 6,190,407 B1 | 2/2001 | Ogle et al. |
| 6,191,337 B1 | 2/2001 | Himmelsbach |
| 6,210,704 B1 | 4/2001 | Sasaki et al. ................ 424/443 |
| 6,224,898 B1 | 5/2001 | Balogh et al. |
| 6,224,983 B1 | 5/2001 | Sodervall et al. |
| 6,245,959 B1 | 6/2001 | Ohira et al. .................. 602/41 |
| 6,248,932 B1 | 6/2001 | Himmelsbach |
| 6,267,743 B1 | 7/2001 | Bodenschatz et al. |
| 6,267,782 B1 | 7/2001 | Ogle et al. |
| 6,274,205 B1 | 8/2001 | Himmelsbach et al. |
| 6,284,328 B1 | 9/2001 | Leydecker et al. |
| 6,322,588 B1 | 11/2001 | Ogle et al. |
| 6,333,093 B1 | 12/2001 | Burrell et al. |
| 6,348,212 B1 | 2/2002 | Hymes et al. |
| 6,350,247 B1 | 2/2002 | Bodenschatz et al. |
| 6,355,858 B1 | 3/2002 | Gibbins |
| 6,383,630 B1 | 5/2002 | Jauchen et al. |
| 6,428,800 B1 | 8/2002 | Greenspan et al. |
| 6,436,420 B1 | 8/2002 | Antelman |
| 6,447,470 B1 | 9/2002 | Bodenschatz et al. |
| 6,459,013 B1 | 10/2002 | Himmelsbach |
| 6,495,230 B1 | 12/2002 | do Canto |
| 6,506,957 B1 | 1/2003 | Himmelsbach et al. |
| 6,524,699 B1 | 2/2003 | Himmelsbach et al. |
| 6,551,704 B1 | 4/2003 | Himmelsbach et al. |
| 6,555,730 B1 | 4/2003 | Albrod et al. |
| 6,569,111 B1 | 5/2003 | Herzberg |
| 6,579,539 B1 | 6/2003 | Lawson et al. |
| 6,582,713 B1 | 6/2003 | Newll et al. |
| 6,592,888 B1 | 7/2003 | Jensen et al. |
| 6,599,525 B1 | 7/2003 | Scamilla Aledo et al. |
| 6,605,751 B1 | 8/2003 | Gibbins et al. |
| 6,617,485 B1 | 9/2003 | Herzberg |
| 6,656,491 B1 | 12/2003 | Brosck et al. |
| 6,695,824 B1 | 2/2004 | Howard et al. |
| 6,706,279 B1 | 3/2004 | Hazzi |
| 6,713,659 B1 | 3/2004 | Bodenschatz et al. |
| 6,716,895 B1 | 4/2004 | Terry |
| 6,730,053 B1 | 5/2004 | Bodenschatz et al. |
| 2001/0055608 A1 | 12/2001 | Hymes et al. |
| 2002/0132545 A1 | 9/2002 | Lenz |
| 2002/0150720 A1 | 10/2002 | Howard et al. |

| | | | |
|---|---|---|---|
| 2002/0156411 | A1 | 10/2002 | Ahrens et al. |
| 2002/0172709 | A1 | 11/2002 | Nielsen et al. |
| 2002/0197257 | A1 | 12/2002 | Meyer-Ingold et al. |
| 2003/0091736 | A1 | 5/2003 | Zschaeck |
| 2003/0170314 | A1 | 9/2003 | Burrell et al. |
| 2003/0176827 | A1 | 9/2003 | Chandra et al. |
| 2003/0185901 | A1 | 10/2003 | Burrell et al. |
| 2003/0194444 | A1 | 10/2003 | Burrell et al. |
| 2003/0203015 | A1 | 10/2003 | Aledo et al. |
| 2004/0002675 | A1 | 1/2004 | Nierle et al. |
| 2004/0009202 | A1 | 1/2004 | Woller |
| 2004/0010215 | A1 | 1/2004 | Gibbins et al. |
| 2004/0058013 | A1 | 3/2004 | Taylor et al. |
| 2004/0086549 | A1 | 5/2004 | Nielsen |
| 2004/0091521 | A1 | 5/2004 | Radloff et al. |

FOREIGN PATENT DOCUMENTS

| | | |
|---|---|---|
| EP | 0128338 | 12/1984 |
| EP | 0254413 | 1/1988 |
| EP | 0291587 | 11/1988 |
| EP | 0 344 090 | 11/1989 |
| EP | 0344090 | 11/1989 |
| EP | 0354315 | 2/1990 |
| EP | 0 367 320 | 5/1990 |
| EP | 0392640 | 10/1990 |
| EP | 1 159 972 | 5/2001 |
| GB | 2127389 | 4/1984 |
| GB | 2188135 | 9/1987 |
| WO | WO 90/08470 | 8/1990 |
| WO | WO 91/11206 | 8/1991 |
| WO | WO 92/13491 | 8/1992 |
| WO | WO 99/15101 | 4/1999 |
| WO | WO 00/25726 | 5/2000 |
| WO | WO 00/73552 | 12/2000 |
| WO | WO 03/022317 | 3/2003 |
| WO | WO 04/002384 | 1/2004 |
| WO | WO 04/037186 | 5/2004 |

OTHER PUBLICATIONS

T. J. Berger, et al., "Antifungal Properties of Electrically Generated Metallic Ions," Antimicrobial Agents and Chemotherapy, vol. 10, pp. 856-860 (1976), USA, 1st named inventor is co-author.

J. A. Spadaro, et al., "Antibacterial Effects of Silver Electrodes With Weak Direct Current," *Antimicrobial Agents and Chemotherapy*, vol. 6, pp. 637-642 (1974), USA, 1st named inventor is co-author.

L. SMEE, "The Effectiveness of Silver Nylon Cloth and Silver Sulfadiazine Cream as Antiseptics," Piedmont College Senior Thesis, Apr., 1996, USA, inventors' files.

U.S. Appl. No. 09/613,961, filed on Jul. 11, 2000, Flick.

Foulds, I.S. and Barker A.T. *Human skin battery potentials and their possible role in wound healing*, British Jorn. of Dermatology, Mar. 1983, 109 pp. 515-522.

Friedenberg Z.B. *Bioelectric Potentials in Bone*. Journ. of Bone and Joint Surgery, Jul. 1966, vol. 48-A, No. 5, pp. 915-923.

Illingworth, C.M and Barker A.T. *Measurement of Electrical Currents Emerging During the Regeneration of Amputated Finger Tips in Children*, Clin. Phys. Physiological Measurements, 1980, vol. 1, No. 1, pp. 87-89.

Jaffe, L.F. and Vanable J.W., Jr. *Electric Fields and Wound Healing*, Clinics in Dermatology, Jul.-Sep. 1984, vol. 2, No. 3, pp. 34-44.

Khanna, A., Sivaraman, R., and Vohora S.B. *Analgesic Activity of Silver Preparations Used in Indian Systems of Medicine*. Indian Journal of Pharmacology, 1997, 29:393-398.

McCaffery M., Pasero C., *Pain: Clinical Manual*, Second Edition, Mosby, pp.62-65.

Ohnhaus E.E. and Adler R. *Methodological Problems in the Measurement of Pain: A Comparison Between the Verbal Rating Scale and the Visual Analouge Scale*, Pain, 1975, Elsevier/North-Holland, Amsterdam, pp. 379-384.

Pain Assessment and Management: An Organizational Approach, Joint Commission, Chapter Three: Assessment of Persons with Pain, (2000), pp. 13-25.

Sriwatanakul K., Kelvie W., Lasagna L., Calimlim, J.F., Weis O.F., Mehta G. *Studies with Different Types of Visual Analog Scales for Measurement of Pain*, Dept. of Pharmacol. Ther., Aug. 1983, pp. 234-239.

Vanable J.W., Jr. *Integumentary Potentials and Wound Healing*, Elec. Fields In Vertebrate Repair, 1989, pp.. 171-224.

Westaim Biomedical Commercial Literature, bearing 1988 Copyright notice and product label bearing Acticoat. RTM.

Partial European Search Report for EP 98 94 9403 dated Jul. 2, 2004.

Complaint—Noble Fiber Technologies, LLC v. Argentum Medical, LLC, Civil Action No. 3:05-CV-01855-ARC, filed Sep. 13, 2005.

US 5,872,068, 02/1999, Cartwright et al. (withdrawn)

* cited by examiner

MULTILAYER WOUND DRESSING

This application is a continuation-in-part of application Ser. No. 08/524,134, filed Sep. 5, 1995, now abandoned, and Ser. No. 08/623,046, filed Mar. 28, 1996, now U.S. Pat. No. 5,814,094.

BACKGROUND OF THE INVENTION

1. Field of the Invention

The present invention relates to a multilayer dressing for the care and treatment of wounds. In particular, the present invention relates to a multilayer dressing having therapeutic and prophylactic properties, and methods for making the dressing.

2. Discussion of Background

The antimicrobial and antifungal properties of silver and silver compounds are well known. Topical preparations that contain silver or silver compounds silver nitrate solution, silver sulfadiazine cream, colloidal silver compositions, silver-protein compounds such as Argyrol™, and so forth—are widely used in medicine. The useful effects of these compositions are due to the small amounts of free silver ions produced by dissociation of the silver compound or to formation of toxic by-products in situ.

The effectiveness of silver as an antimicrobial agent is at least partly determined by the delivery system. Most silver compounds that dissociate readily and produce large numbers of free silver ions are highly toxic to mammalian (including human) tissues. Less-toxic compounds, including silver sulfadiazine cream (widely used in the treatment of burns) and silver nitrate solution, do not dissociate readily and therefore do not release large numbers of silver ions. These compounds must be re-applied frequently to maintain their clinical efficacy.

Electrically-generated silver ions, which can penetrate more deeply into the tissues, are effective even against antibiotic-resistant strains of bacteria, fungi, etc., inhibiting growth in vivo and in vitro at current densities as low as 10 nA/mm$^2$ and silver ion concentrations as low as 0.5 mg/ml. The effects of electrically-generated silver ions are described in a number of publications, including the following: J. A. Spadaro, et al., "Antibacterial Effects of Silver Electrodes with Weak Direct Current," *Antimicrobial Agents &Chemotherapy*, Vol. 6, pp. 637–642 (1974); T. J. Berger, et al., "Antifungal Properties of Electrically Generated Metallic Ions," *Antimicrobial Agents &Chemotherapy*, Vol. 10, pp. 856–860 (1976); R. O. Becker, et al., "Treatment of Orthopedic Infections With Electrically-Generated Silver Ions," *J. Bone &Joint Surgery*, Vol. 60-A, pp. 871–881 (1978)).

Silver and other metals are widely used in wound dressings and materials therefor. Fabo (U.S. Pat. No. 5,340,363) discloses a dressing that includes an outer absorbent layer and an inner porous, hydrophobic layer knitted of elastic threads and encapsulated by a soft, hydrophobic silicone or polyurethane gel. The gel can be used as a carrier for antibacterial agents such as zinc, pain-relieving substances, and agents that stimulate wound repair. Klippel, et al. (U.S. Pat. No. 3,830,908) use micronized allantoin as a carrier for a bactericidal or bacteristatic ingredient (such as silver citro allantoinate) that is dispersed on the surface of a plastic air splint or other bandaging product. McKnight, et al. (U.S. Pat. No. 3,800,792) disclose a surgical dressing having a layer of tanned, reconstituted collagen foam film laminated to a thin, continuous layer of an inert polymer. The collagen layer contains finely-divided silver metal added by soaking the collagen film in Tollen's reagent. Stowasser (U.S. Pat. No. 2,934,066) makes a dressing of absorbent, metal-coated fibers, such as a carding fleece coated with aluminum and backed by compressed cellulose, and polyamide fibers coated with vacuum-deposited silver.

Dressings for provision of electrical stimulation are also known. For example, Jones (U.S. Pat. No. 4,911,688) covers a wound with a clear cover that serves as a hollow chamber for holding a fluid such as saline in contact with a wound. When connected to a voltage source, a metal anode and a return electrode create free ions and an electrical field to enhance healing and tissue regeneration. Juhasz (U.S. Pat. No. 4,817,594) discloses a multi-layer dressing for covering discharging, malodorous wounds. The dressing includes a layer of an electrically-conductive material such as silver and a layer of charcoal fabric. Application of a DC (direct current) voltage to the conductive layer drives silver ions into the wound to enhance tissue growth and inhibit bacterial growth; application of transcutaneous AC (alternating current) is used for post-operative pain relief Seiderman (U.S. Pat. No. 4,767,401) describes a bandage like device used for iontophoretic administration of medicaments, including silver-protein colloids. The device includes a metal foil electrode (preferably aluminum), and makes use of the slight inherent negative electric charge proximate a wound site to generate a small electric field at the site.

Matson (U.S. Pat. No. 4,728,323) coats a substrate (nylon fabric, polymeric film, fiberglass, gauze or polyurethane foam) with a film of a silver salt deposited by vapor or sputter coating techniques. Alternatively, fibers can be coated and then woven or knitted into a fabric. Konikoff (U.S. Pat. No. 4,142,521) shows a bandage or surgical sponge material incorporating one or more electret elements, each electret providing a small electrostatic field to the area of the wound.

In U.S. Pat. No. 5,814,094, Becker, et al. disclose a bimetallic fabric woven of nylon fibers coated with a first metal such as silver, interspaced at intervals with fibers coated with a second metal such as gold or platinum, preferably in a ratio of about 10:1. Alternatively, deposits of the second metal are placed on a fabric that contains the first metal. When contacted with an electrolyte, each contact junction between the first and second metals serves as a bimetallic junction that produces free silver ions. The material may be used in therapeutic or prophylactic treatment of wounds (including surgical incisions). An iontophoretic system for promoting tissue healing processes and inducing regeneration is described in application Ser. No. 08/623,046, filed Mar. 28, 1996. The system is implemented by placing a flexible, silver-containing anode in contact with the wound, placing a cathode on intact skin near the anode, and applying a wound-specific DC voltage between the anode and the cathode. Electrically-generated silver ions from the anode penetrate into the adjacent tissues and undergo a sequence of reactions leading to formation of a silver-collagen complex. This complex acts as a biological inducer to cause the formation in vivo of an adequate blastema to support regeneration. The disclosures of the above-referenced patent applications are incorporated herein by reference.

Regardless of whether silver is provided in the form of silver ions or as a topical composition (silver nitrate solution, silver sulfadiazine cream, etc.), its beneficial effects are manifested primarily at the treated surface and immediately adjacent tissues, and are limited by the achievable tissue concentration of silver ions. Despite the availability of numerous techniques for the delivery of silver and silver compounds in vitro and in vivo, there remains a need for a delivery system that is capable of supplying clinically useful concentrations of silver ions to a treatment site without the need for adjuvant electrical stimulation.

SUMMARY OF THE INVENTION

According to its major aspects and broadly stated, the present invention is a flexible, multilayer dressing for therapeutic and prophylactic use, together with methods for making the dressing. The dressing includes a layer of fabric that contains a metal having bactericidal/bacteristatic properties, a layer of absorbent material, and, optionally, a layer of air-permeable and/or water-impermeable material. (For purposes of this description, a metal with "bactericidal properties" and/or "bacteristatic properties" is broadly defined as a metal that is active against at least one type of pathogenic agent, including bacteria, protozoa, fungi, rickettsiae, and viruses. Bactericidal agents kill organisms, whereas bacteristatic agents prevent their growth and multiplication.)

The multilayer dressing is used in the care and treatment of skin infections and surface wounds (including surgical incisions), as a packing material for deep wounds, and as a swab for surface cleaning. In use, the dressing is effective in preventing the growth of pre-existing bacterial and fungal contaminants (particularly in traumatic wounds), and as a prophylactic measure against airborne contaminants (bacteria, fungi, etc.) and opportunistic infections.

A major feature of the present invention is the inner layer of the dressing, which contacts the wound surface when in use. The inner layer contains a bactericidal/bacteristatic metal (preferably silver) loosely bound to a flexible, conformable fabric substrate. When the fabric is placed on the treatment site and contacted by saline, wound exudate, or water, at least a portion of the metal is released into the surrounding tissues with resulting beneficial effects. The inner layer may be made of metallized fibers of any suitable material, for example, it may be knitted or woven of silver-coated nylon fibers. Such a fabric is durable, nontoxic, nonhazardous, and inert until activated by contact with a suitable liquid.

An important feature of the present invention is the multilayer dressing itself In a preferred embodiment of the invention, the dressing includes at least two layers: an inner layer of silver-containing fabric and a layer of moisture-absorbing material. Both layers are sufficiently flexible to conform to the area being treated, and can be provided in sizes and thicknesses suitable for the intended use. In this form, the dressing can be applied to surface wounds such as cuts (including surgical incisions), scrapes, and burns. It can also be applied to intact skin to treat localized infections, or used to pack deep wound cavities. For surface applications, the multilayer material may include a third, outer layer of an air-permeable and/or water-impermeable material. If desired, a layer of a suitable adhesive can be added to adhere the dressing to the skin.

Another feature of the present invention is the method for making the dressing, which can be adapted for a variety of end uses. The dressing may be made by any convenient techniques known in the art, of readily available, generally inexpensive materials. It may be provided in a convenient form for a variety of applications, ranging from individual BANDAID-type dressings to rolls or sheets that can be cut to any needed size. For example, a two-layer dressing approximately 4" wide by 3' long (about 10×90 cm), wherein the absorbent layer is no more than approximately 2–3 times as thick as the silver fabric layer, is useful for packing deep wound cavities. On the other hand, a three-layer dressing with an air-permeable outer layer may be preferred for a burn or a surgical incision.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
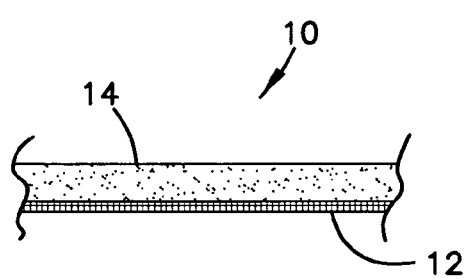
FIG. 1 is a cross-sectional view of a multilayer dressing according to a preferred embodiment of the present invention.

In the following detailed description, reference numerals are used to identify structural elements, portions of elements, surfaces and areas in the drawings. For consistency, whenever the same numeral is used in different drawings, it indicates the same element, portion, surface and area as when first used.

Referring now to FIG. 1, there is shown a cross-sectional view of a multilayer material 10 according to a preferred embodiment of the present invention. Multilayer material 10 includes a first layer 12 of silver-containing fabric and a second layer 14 of a moisture-absorbent material.

First layer 12 consists of a flexible, conformable metallized fabric made by weaving, knitting, crocheting, felting, blowing, or some other convenient process. Preferably, first layer 12 is made of silver-coated nylon fibers. However, other materials may also be suitable, including nonwoven sheet material that incorporate or are coated with suitable amounts of silver.

Silver (or some other metal with medically useful bactericidal/bacteriostatic properties) may be added to the fibers of layer 12 by vapor coating, aerosolized deposition, sputter coating or other standard techniques known in the art. Individual fibers can be coated and then worked (woven, knitted, crocheted, felted, blown, etc.) into a fabric. Alternatively, suitable amounts of silver may be added to the finished fabric. While the thickness of such a silver coating may vary broadly, the amount of silver should be such that layer 12 has a specific resistance no greater than approximately 5 $\Omega$/cm; most preferably, layer 12 has a specific resistance no greater than approximately 1 $\Omega$/cm. Typically, a medically-useful material for layer 12 contains at least approximately 5 wt. % silver, preferably approximately 20 wt. % silver. However, the metal content and specific resistance of layer 12, as well as the thickness and uniformity of the coating, may vary broadly depending on the selected metal and the intended uses of dressing 10. Thus, fabrics with lesser amounts of metal may also be useful in the practice of the invention. Materials with higher resistance (and lower silver content) may also be useful; however, such materials will generally be incapable of supplying the needed amounts of free silver to the treatment site.

Layer 12 should also not only be made of a material having a sufficiently high content of silver (or other suitable metal), but the silver should be approximately uniformly distributed. Non-uniform distribution means that the wound will not be uniformly treated: the amount of silver supplied to different areas will differ.

The silver in layer 12 is releasably attached to the fabric substrate so that, when layer 12 is placed in contact with body tissues and moistened by a suitable liquid, at least a portion of the silver migrates into the adjacent tissues. While not wishing to be bound by theory, it is believed that metallized fabrics wherein the metal atoms are somewhat loosely bound to the molecules of the fabric substrate (forming a chemical or physical complex with the substrate rather than being simply deposited onto it) are especially suitable for the practice of the present invention. In a complex of this nature, the bond energy is sufficiently low to permit effusion of the metal when the fabric is wet.

Second layer 14 is made of a soft, flexible, moisture-absorbent material capable of seeping up wound exudates, such as woven or nonwoven cotton (layer 14 may be moistened with water, normal saline, or other suitable liquid when dressing 10 is in use). Layer 14 need be no more than approximately 0.1–0.5 cm thick; however, thicker layers may be useful when material 10 is used in the care of draining wounds.

Multilayer material 10 is inert until moistened by water, wound exudate, normal saline, or other liquid. Then, the bonds between the silver atoms and the fabric substrate of first layer 12 are loosened and at least some of the silver migrates from the fabric into the surrounding tissues. When placed on a wound with first layer 12 contacting the body surface, naturally-occurring body fluids may be sufficient to activate material 10. However, a suitable liquid (normal saline, Ringer's solution, tap water and the like) must generally be applied to ensure release of silver from layer 12.

Figure 2:
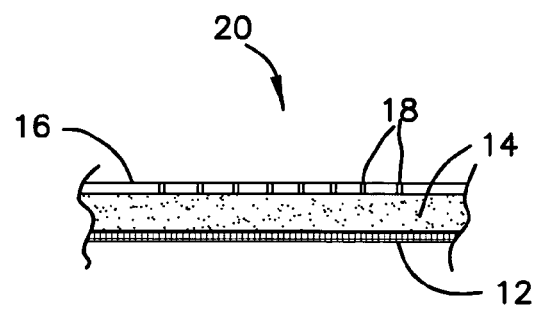
FIG. 2 is a cross-sectional view of a multilayer dressing according to another preferred embodiment of the invention.

Another multilayer material according to the present invention is shown in FIG. 2. A material 20, like above-described material 10, includes a metal-containing layer 12 and a moisture-absorbing layer 14. Adjacent to layer 14 is a thin, flexible outer layer 16 made of nonporous plastic material, with a plurality of perforations 18 therethrough. Outer layer 16 may be made of an air-permeable, moisture-impermeable material such as GORETEX. Alternatively, layer 16 may be a plastic material such as the materials used in commercially-available dressings (BANDAID, CURAD, etc.).

Figure 3:
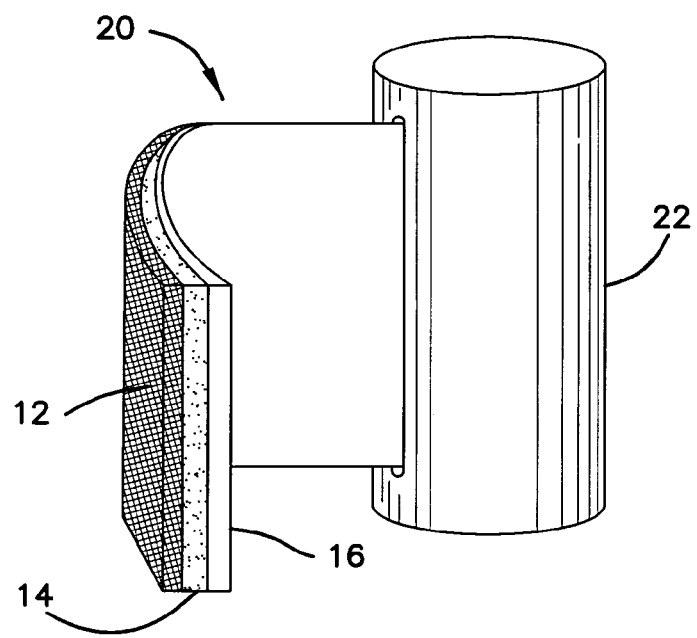
FIG. 3 is a perspective view of the multilayer dressing of FIG. 2, shown packed in a dispenser.

Materials 10 and 20 may be furnished in dimensions to suit various applications, for example, 2" (about 5 cm) widths for covering surgical incisions and relatively small wounds, and 12" (about 30 cm) or larger widths for covering large wounds such as burns, and cut to any needed length. When made in sections approximately 4"×3' (about 10×90 cm) and with an absorbent layer 14 no thicker than approximately 2–3 times the thickness of layer 12, material 10 is useful as a packing material for deep wounds. Material 20 (or material 10) may be packed in a dispenser 22 for shipping, storage, and eventual use (FIG. 3).

Materials 10 and 20 may be used in a variety of wound dressings to provide prophylactic and/or therapeutic activity to help prevent (or treat) infection and facilitate healing. The dimensions and configuration of such dressings depend on the size and location of the area to be treated, and requires a means for affixing the dressing in place, controlling moisture loss from the wound, and ensuring direct contact between the layer 12 and the actual wound surface itself.

Figure 4:
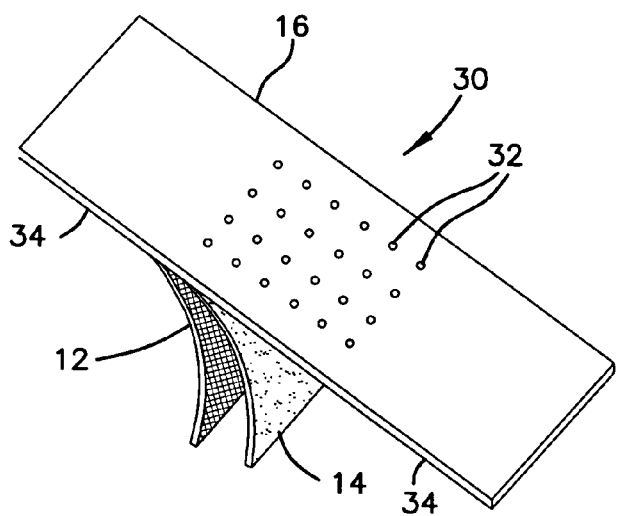
FIG. 4 is a perspective view of another multilayer dressing according to the invention.

A wound dressing 30 according to the present invention is shown in FIG. 4. Dressing 30 includes a thin, flexible outer layer 16, an absorbent layer 14 attached to the medial portion of layer 16, and at least one inner layer 12 of silver-containing fabric (layers 12 and 14 are shown pulled away from layer 16 for clarity). Perforations 32 in the medial portion of layer 16 provided added ventilation on the wound surface to assist in epitheliazation. An inner side 34 of layer 16, on either side of layers 12, 14, may be coated with an adhesive and protected with a removable strip of material (not shown) that is peeled off just prior to use. Dressing 30 is flexible and, via the adhesive coating on layer 32, capable of adhering to dry skin. In use, wound exudate (or some other liquid) moistens layer 12 and passes therethrough to absorbent, moisture-retaining layer 14.

Figure 5:
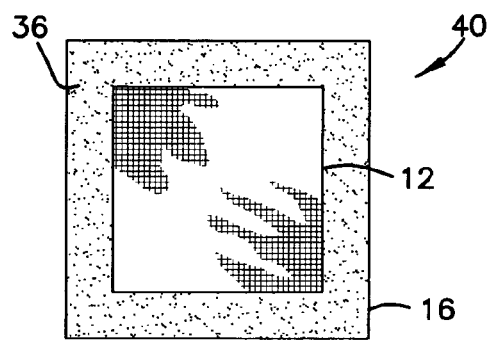
FIGS. 5–7 are plan views of additional multilayer dressings according to the invention.
Figure 6:
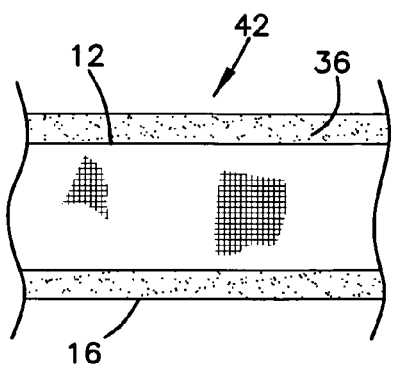

Another wound dressing 40 is shown in FIG. 5. Dressing 40 is made of material 20, thus, includes a silver-containing layer 12, an absorbent layer 14 (not shown), and an outer layer 16 having a larger area than layer 12. A layer of adhesive 36 coats the inner side of layer 16, generally as shown. A dressing 42 with adhesive margins 36 may be furnished in a strip of any convenient length (FIG. 6). Adhesive 36 may be covered by a peel-off strip (not shown) prior to use. Dressings 40, 42 may, of course, be made in any convenient sizes.

Figure 7:
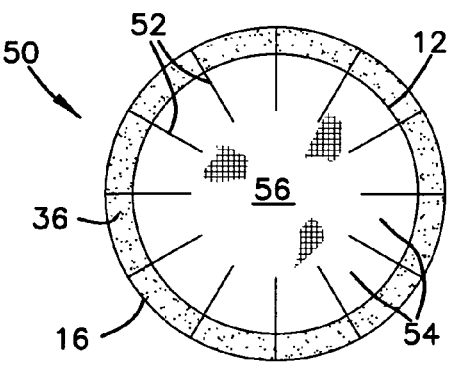

A wound dressing 50 adapted for placement on fingertip wounds is shown in FIG. 7. Dressing 50, like dressing 40, is made of material 20 and has an outer layer 16 that is larger in area than silver-containing layer 12 and a layer of adhesive 36 coating the inner side of layer 16. A plurality of radial slits 52 extend inwards from the periphery of dressing 50, to form a series of flaps 54 about a central portion 56. Dressing 50 preferably has at least four slits 52 forming four flaps 54. However, a greater number of slits 52, such as the twelve slits 52 at approximately 30° intervals shown in FIG. 7, are preferred.

In use, portion 56 is centered on the fingertip with layer 12 adjacent to the skin. Flaps 54 are affixed to the skin by adhesive 36, distal to wound. By overlapping flaps 54, the user can form dressing 50 into a "cap" that covers the fingertip. While human digits vary widely in size, a dressing 50 approximately 2" (about 5 cm) in diameter with a central portion 56 approximately 1" (about 2.5 cm) in diameter is suitable for most. However, dressing 50 can easily be made in different sizes to better fit very small or very large digits.

Multilayer materials 10, 20 (and dressings made with the materials) are flexible, easily re-shapable and conformable to the region to be treated. Materials 10, 20 can be used for treating surface wounds such as cuts, scrapes, and burns, and also be used for filling in deep wound cavities, thereby enabling the wound edges to be kept apart during the healing process.

In use, materials 10, 20 (or dressings such as dressings 30, 40, 42, 50) are applied to the skin after appropriate surface preparation (dressings 30, 40, 42 are preferably applied to dry skin so that adhesive 36 adheres well to the skin to hold the dressing in place). Depending on the area to be treated, the layers 12, 14 may be moistened to stimulate release of silver from the material. Silver is released from layer 12 and migrates into the area to minimize external and cross-contamination of the treatment site, and help prevent bacterial and fungal infections, while not hindering normal cell growth or repair. No toxic substance is introduced into the patient's body. Materials 10, 20 (and dressings that contain these materials) are preferably replaced daily; however, the materials can be safely left in place for as long as 3 days if circumstances so require. The materials can be used for prophylactic treatment of fresh wounds and surgical incisions, treatment or prevention of early stage decubital ulcers ("bed sores"), therapeutic treatment of infected and traumatic wounds, and so forth.

The present invention is further illustrated in the following nonlimiting examples.

EXAMPLE 1

The effectiveness of warp knit silver nylon fabric (specific resistance about 1 Ω/cm) in inhibiting the growth of three common strains of bacteria (*S. aureus, E. coli* and *P. aeruginosa*) was tested in vitro. The bacterial cultures were planted in agar-filled petri dishes using the Kirby Bauer technique, one culture per dish. Sterilized 1-cm squares of the fabric were placed on the surfaces of the cultures. Every twenty-four hours, each fabric square was removed from the culture medium and replanted in a different area of the same dish. After 72 hours, the culture medium directly underneath the fabric squares was clear (i.e., the bacteria in those regions had been killed). In addition, all areas where the fabric squares had been placed previously remained clear.

EXAMPLE 2

The warp knit silver nylon fabric of Example 1 was found to cause dedifferentiation of mammalian cells in vitro. The observed effects were proportional to the concentration of silver ions in the culture medium and inversely proportional to distance from the fabric: the closer to the fabric, the greater the concentration of dedifferentiated cells and the greater the silver ion concentration.

EXAMPLE 3

The effectiveness of silver sulfadiazine cream, silver nylon fabric, and plain nylon fabric in inhibiting the bacterial growth was compared (L. Smee, "The Effectiveness of Silver Nylon Cloth and Silver Sulfadiazine Cream as Antiseptics," Piedmont College Senior Thesis, April, 1996). Five common strains of bacteria were studied including two gram-negative strains (*E. coli, P. aeruginosa*) and three gram-positive strains (*E. faecalis, S. aureus, S. pyogenes*).

Each strain of bacterium was inoculated into three agar-filled petri dishes. Following the inoculation, three fabric disks were placed into each dish: a disk of plain nylon cloth which served as a control, a disk of silver nylon fabric, and a plain nylon disk which has been coated with silver sulfadiazine cream. Each disk had a surface area of 3.4 mm². The dishes were incubated for seventy-two hours, and removed every twenty-four hours to measure the inhibition zone around each disk (i.e., the distance from the outer edge of the fabric disk to the perimeter of the clear zone of inhibited bacterial growth about the disk).

Results indicated that the silver nylon fabric and silver sulfadiazine cream were effective bacterial growth inhibitors against all tested strains. Average results for two trials are listed in Table I.

Table I. Inhibition zones (mm) for silver nylon fabric (Ag Nylon), nylon fabric with silver sulfadiazine cream (Nylon+Ag Cream), and plain nylon fabric (Nylon). Results shown represent the average of two trials.

TABLE I

Inhibition zones (mm) for silver nylon fabric (Ag Nylon), nylon fabric with silver sulfadiazine cream (Nylon + Ag Cream), and plain nylon fabric (Nylon). Results shown represent the average of two trials.

|  | Ag Nylon | Nylon + Ag Cream | Nylon |
|---|---|---|---|
| *E. coli* | | | |
| Day 1 | 7.4 | 6.3 | 0 |
| Day 2 | 9.2 | 6.4 | 0 |
| Day 3 | 10 | 7.2 | 0 |
| *P. aeruginosa* | | | |
| Day 1 | 57 | 32 | 0 |
| Day 2 | 59 | 29 | 0 |
| Day 3 | 62 | 29 | 0 |
| *E. faecalis* | | | |
| Day 1 | 8.9 | 4.0 | 0 |
| Day 2 | 11 | 3.8 | 0 |
| Day 3 | 15 | 2.4 | 0 |
| *S. aureus* | | | |
| Day 1 | 9.3 | 7.1 | 0 |
| Day 2 | 9.5 | 2.1 | 0 |
| Day 3 | 12 | 0.9 | 0 |
| *S. pyogenes* | | | |
| Day 1 | 57 | 28 | 0 |
| Day 2 | 66 | 34 | 0 |
| Day 3 | 70 | 38 | 0 |

These results indicate that silver nylon fabric is an effective antimicrobial agents. In Example 3, the fabric proved to be more effective than silver sulfadiazine cream, creating and maintaining a larger inhibition zone for each strain tested for the duration of the experiments.

As a delivery system for silver, a fabric with a sufficiently high concentration of silver releases silver ions at a steady rate for as long as the fabric is in contact with the culture medium (in vitro or in vivo). Such a fabric does not cause allergic reactions, thus, its use prevents other potentially-harmful side effects associated with other delivery systems (silver sulfadiazine, silver thiosulfate). A multilayer dressing using the fabric is nonhazardous, conformable to the shape of the site to be treated, readily adaptable to diverse clinical situations, and safe and easy to use. When treating patients with extensive burns, a dressing according to the invention is less expensive, less cumbersome, and more effective than silver sulfadiazine cream.

It will be apparent to those skilled in the art that many changes and substitutions can be made to the preferred embodiment herein described without departing from the spirit and scope of the present invention as defined by the appended claims.

The invention claimed is:

1. A wound dressing comprising:
   at least one conformable layer comprising woven fibers uniformly and individually coated with an amount of an anti-microbial metal sufficient to provide the conformable layer with a specific resistance no greater than approximately 5 ohms/cm².

2. The wound dressing of claim 1, wherein the anti-microbial metal comprises silver.

3. The wound dressing of claim 2, wherein the silver is releasably attached to said fibers.

4. The wound dressing of claim 1, wherein the conformable layer has a specific resistance of no greater than approximately 1 ohm/cm².

5. The wound dressing of claim 1, wherein the conformable layer comprises at least approximately 5 wt. % silver.

6. The wound dressing of claim 1, wherein the fibers comprise cotton or nylon.

7. The wound dressing of claim 1, further comprising a second layer.

8. The wound dressing of claim 7, wherein the second layer comprises a moisture-absorbent material.

9. The wound dressing of claim 1, wherein the wound dressing causes dedifferentiation of mammalian cells.

10. The wound dressing of claim 1, wherein the wound dressing inhibits bacterial growth.

11. The wound dressing of claim 10, wherein the wound dressing inhibits *E. coli, P. aeruginosa, E. faecalis, S. aureas,* or *S. pyrogenes*.

12. A method of treating a wound comprising applying the wound dressing of claim 1 to the wound.

13. A wound dressing comprising:
   a conformable fabric comprising woven fibers uniformly and individually coated with an amount of silver sufficient to provide the conformable fabric with a specific resistance no greater than approximately 1 ohm/cm$^2$.

* * * * *

UNITED STATES PATENT AND TRADEMARK OFFICE
CERTIFICATE OF CORRECTION

| | | |
|---|---|---|
| PATENT NO. | : 7,005,556 B1 | Page 1 of 1 |
| APPLICATION NO. | : 08/707779 | |
| DATED | : February 28, 2006 | |
| INVENTOR(S) | : Robert O. Becker, A. Bartholomew Flick and Adam J. Becker | |

It is certified that error appears in the above-identified patent and that said Letters Patent is hereby corrected as shown below:

Cover page, Item (63), under "Related U.S. Application Data", replace
"Continuation-in-part of application No. 08/524,134, filed on Sep. 5, 1995, now abandoned, which is a continuation-in-part of application No. 08/623,046, filed on Mar. 28, 1996, now Pat. No. 5,814,094."
with
--Continuation-in-part of application No. 08/623,046, filed on Mar. 28, 1996, now Pat. No. 5,814,094, which is a continuation-in-part of application No. 08/524,134, filed on Sep. 5, 1995, now abandoned.--

Signed and Sealed this
Twenty-seventh Day of November, 2012

David J. Kappos
*Director of the United States Patent and Trademark Office*